US012755413B2

(12) United States Patent
Kurokawa

(10) Patent No.: US 12,755,413 B2
(45) Date of Patent: Oct. 6, 2026

(54) MEDICAL IMAGE PROCESSING APPARATUS, CONTROL METHOD, AND PROGRAM FOR ELIMINATING DISCREPANCIES BETWEEN DISPLAY CONTENTS AND HISTORY DATA WHEN CORRECTING A MEASUREMENT VALUE

(71) Applicant: Konica Minolta, Inc., Tokyo (JP)

(72) Inventor: Shinya Kurokawa, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 359 days.

(21) Appl. No.: 18/326,516

(22) Filed: May 31, 2023

(65) Prior Publication Data

US 2023/0419528 A1 Dec. 28, 2023

(30) Foreign Application Priority Data

Jun. 23, 2022 (JP) ................................ 2022-101313

(51) Int. Cl.
*G06T 7/60* (2017.01)
*G06T 5/50* (2006.01)
(Continued)

(52) U.S. Cl.
CPC .................. *G06T 7/60* (2013.01); *G06T 5/50* (2013.01); *G16H 15/00* (2018.01); *G16H 30/40* (2018.01); *G06T 2207/20221* (2013.01)

(58) Field of Classification Search
CPC ... G06T 7/60; G06T 5/50; G06T 2207/20221; G16H 15/00; G16H 30/40; A61B 8/468; A61B 8/463
See application file for complete search history.

(56) References Cited

U.S. PATENT DOCUMENTS 9,846,938 B2 * 12/2017 Steigauf ............... G06V 10/451
10,445,462 B2 * 10/2019 Sorenson ................ G06F 40/30
(Continued)

FOREIGN PATENT DOCUMENTS

JP 2010233879 A 10/2010
JP 2021029538 A 3/2021
WO WO-2022049868 A1 * 3/2022 ............... G09G 3/36

OTHER PUBLICATIONS

Office Action, dated Nov. 4, 2025, which was issued for the corresponding Japanese Patent Application No. 2022-101313, 6 pages, with English translation.
(Continued)

*Primary Examiner* — Mia M Thomas
(74) *Attorney, Agent, or Firm* — LUCAS & MERCANTI, LLP

(57) ABSTRACT

A medical image processing apparatus includes a hardware processor that displays a measurement image including a measurement object and a measurement scale for measuring a measurement value related to the measurement object in a manner that the measurement scale is superimposed on the measurement image, manages history information related to the measurement value, and accepts correction or deletion of a position of the measurement scale, wherein the hardware processor corrects or deletes a history measurement value corresponding to the measurement scale having the position corrected or deleted among history measurement values included in the history information in a case where the position of the measurement scale is corrected or deleted.

10 Claims, 11 Drawing Sheets

(51) Int. Cl.

| | |
|---|---|
| ***G16H 15/00*** | (2018.01) |
| ***G16H 30/40*** | (2018.01) |

(56) References Cited

U.S. PATENT DOCUMENTS

| | | | | |
|---|---|---|---|---|
| 11,024,406 | B2 * | 6/2021 | Sadeghi | G06Q 10/10 |
| 11,801,114 | B2 * | 10/2023 | Lang | A61B 90/37 |
| 2016/0147946 | A1 * | 5/2016 | Von Reden | G16H 10/60 705/3 |
| 2016/0251030 | A1 * | 9/2016 | Okada | G06T 1/0007 345/633 |
| 2016/0350919 | A1 * | 12/2016 | Steigauf | G16H 40/20 |
| 2018/0101645 | A1 * | 4/2018 | Sorenson | G06V 30/19167 |
| 2021/0158105 | A1 * | 5/2021 | Machida | G06V 10/7784 |
| 2021/0271914 | A1 * | 9/2021 | Keshwani | G06T 7/0012 |
| 2024/0054645 | A1 * | 2/2024 | Higa | G16H 30/40 |
| 2024/0078637 | A1 * | 3/2024 | Yang | A61B 8/0841 |

OTHER PUBLICATIONS

Office Action, issued on Apr. 28, 2026 for the corresponding Japanese Patent Application No. 2022-101313, 6 pages, with English translation.

* cited by examiner

| | 1st | 2nd | 3rd | 4th | 5th |
|---|---|---|---|---|---|
| EFW | 496g | | | | |
| GS | 35.4mm | | | | |
| CRL | 29.0mm | 20.0mm | | | |

301

BPD : 14.7mm
AC : 149.4mm
EFW : 496g
GS : 35.4mm
CRL1 : 29.0mm
CRL2 : 20.0mm

203

MEDICAL IMAGE PROCESSING APPARATUS, CONTROL METHOD, AND PROGRAM FOR ELIMINATING DISCREPANCIES BETWEEN DISPLAY CONTENTS AND HISTORY DATA WHEN CORRECTING A MEASUREMENT VALUE

The entire disclosure of Japanese patent Application No. 2022-101313, filed on Jun. 23, 2022, is incorporated herein by reference in its entirety.

BACKGROUND

Technological Field

The present disclosure relates to a medical image processing apparatus, a control method, and a program.

Description of the Related Art

As an example of a medical image diagnostic apparatus, an ultrasonic image diagnostic apparatus that transmits an ultrasonic wave to a subject, receives and processes an echo signal of it, and generates an ultrasonic image is widely used.

For example, in an ultrasonic image diagnostic apparatus described in JP 2021-029538 A, a first display area for displaying an ultrasonic image and a measurement cursor for measurement and a second display area for displaying a measurement value measured by the measurement cursor are displayed on an inspection screen. Then, in the ultrasonic image diagnostic apparatus described in JP 2021-029538 A, when the inspector performs an operation of correcting any one of the measurement values displayed in the second display area, the display of the measurement value displayed in the second display area is corrected, and the display position of the measurement cursor in the first display area is corrected.

In addition, in the ultrasonic image diagnostic apparatus described in JP 2021-029538 A, when the measurement value displayed in the second display area is corrected, the corresponding measurement value included in the report that can output the measurement result is also corrected.

Incidentally, when measurement is performed using a medical image diagnostic apparatus or the like, it is generally performed to improve reliability of an inspection result by storing history data of measurement values.

In the ultrasonic image diagnostic apparatus disclosed in JP 2021-029538 A, in a case where history data of measurement values is stored, for example, in a case where a measurement value displayed in the second display area is corrected, there may be a problem that the measurement value displayed in the second display area and the measurement value included in the report are different from the measurement value remaining in the history data.

SUMMARY

The present disclosure has been made in view of such circumstances, and an object of it is to provide a medical image processing apparatus, a control method, and a program capable of eliminating discrepancy between the display contents and the history data at the time of correcting the measurement value.

To achieve the abovementioned object, according to an aspect of the present invention, a medical image processing apparatus reflecting one aspect of the present invention comprises a hardware processor that displays a measurement image including a measurement object and a measurement scale for measuring a measurement value related to the measurement object in a manner that the measurement scale is superimposed on the measurement image, manages history information related to the measurement value, and accepts correction or deletion of a position of the measurement scale, wherein the hardware processor corrects or deletes a history measurement value corresponding to the measurement scale having the position corrected or deleted among history measurement values included in the history information in a case where the position of the measurement scale is corrected or deleted.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
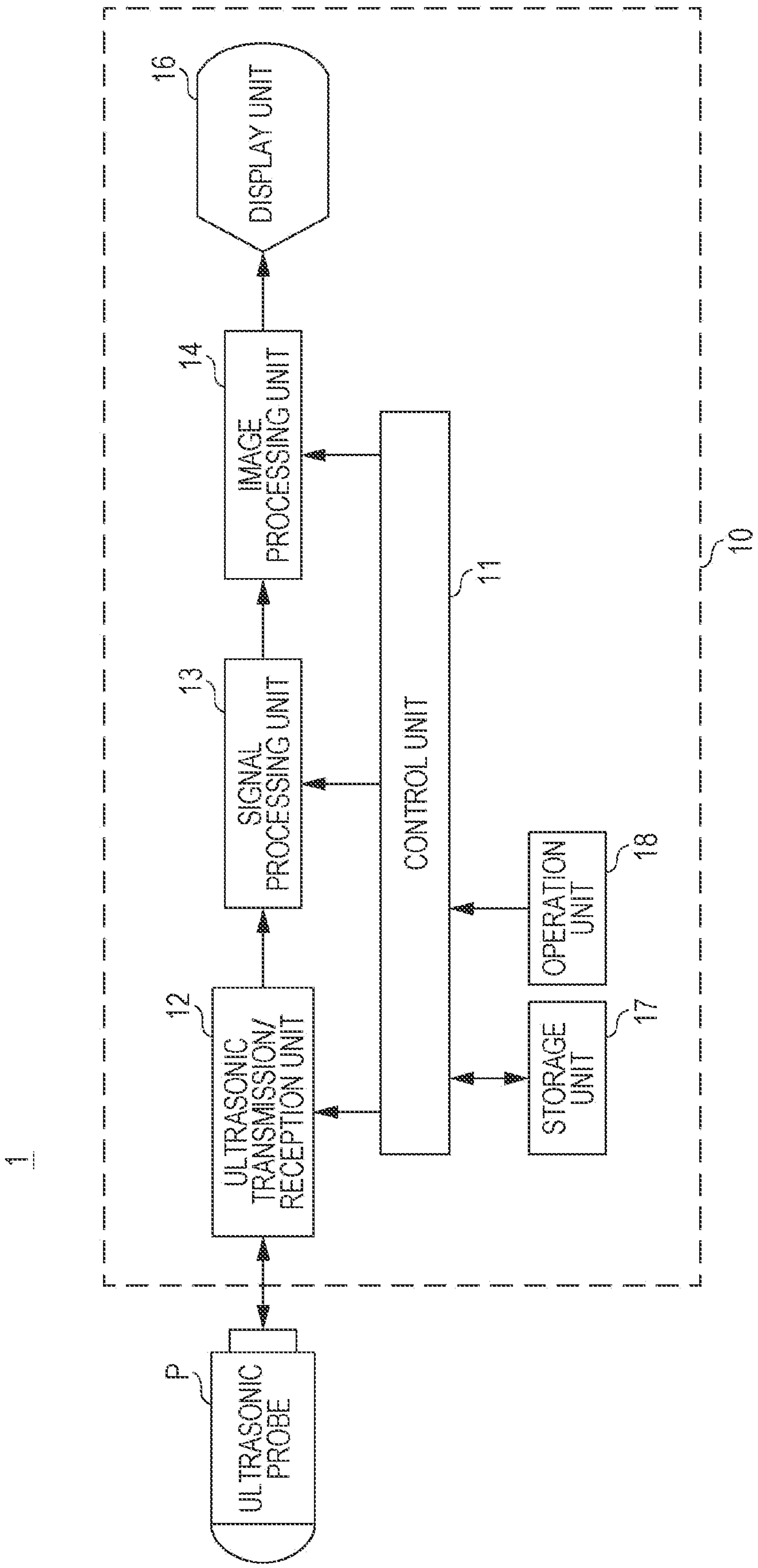
FIG. 1 is a block diagram illustrating a configuration of an ultrasonic diagnostic apparatus according to an embodiment of the present disclosure.

Hereinafter, one or more embodiments of the present invention will be described with reference to the drawings. However, the scope of the invention is not limited to the disclosed embodiments. Note that, in the following description, components having the same functions and configurations are denoted by the same reference numerals, and the description will be omitted.

FIG. 1 is a block diagram illustrating a configuration of an ultrasonic diagnostic apparatus 1 according to an embodiment of the present disclosure.

As illustrated in FIG. 1, the ultrasonic diagnostic apparatus 1 includes an ultrasonic diagnostic apparatus main body 10 and an ultrasonic probe P.

The ultrasonic probe P transmits an ultrasonic wave to a subject such as a living body (not illustrated) and receives a reflection wave (reflection echo) of the ultrasonic wave reflected by the subject. Then, the ultrasonic probe P acquires a reception signal which is an electric signal from the received reflection echo and outputs the reception signal to the ultrasonic diagnostic apparatus main body 10.

The ultrasonic diagnostic apparatus main body 10 is connected to the ultrasonic probe P via a cable or the like. The ultrasonic diagnostic apparatus main body 10 transmits a transmission signal of an electric signal to the ultrasonic probe P to cause the ultrasonic probe P to transmit an ultrasonic wave to the subject. In addition, the ultrasonic diagnostic apparatus main body 10 images and displays the internal state of the inside of the subject as an ultrasonic image based on the reception signal received from the ultrasonic probe P.

As illustrated in FIG. 1, the ultrasonic diagnostic apparatus main body 10 includes a control unit 11, an ultrasonic transmission/reception unit 12, a signal processing unit 13, an image processing unit 14, a frame memory (not illustrated), a display unit 16, a storage unit 17, an operation unit 18, or the like.

The control unit 11 controls the entire ultrasonic diagnostic apparatus 1. The control unit 11 is a processor including, for example, a central processing unit (CPU), a random access memory (RAM), or the like. The control unit 11 executes various processings in cooperation with various programs stored in the storage unit 17 to integrally control the operation of the ultrasonic diagnostic apparatus 1.

The ultrasonic transmission/reception unit 12 supplies a transmission signal to the ultrasonic probe P and causes the ultrasonic probe P to generate an ultrasonic wave. In addition, the ultrasonic transmission/reception unit 12 receives a reflection echo generated in the subject by the ultrasonic probe P, generates a reception signal, and outputs the reception signal to the signal processing unit 13.

The signal processing unit 13 electrically amplifies the reception electrical signal obtained by converting the reception signal, performs signal processing such as digital conversion, and outputs the signal to the image processing unit 14.

The image processing unit 14 generates an ultrasonic image (for example, the B-mode image) based on the digital reception signal output from the ultrasonic transmission/reception unit 12. The B-mode image represents the intensity of the reception signal by luminance. The ultrasonic image generated by the image processing unit 14 is stored in the frame memory in units of frame images. When the ultrasonic image is output from the image processing unit 14, the control unit 11 overwrites the output ultrasonic image in the frame memory in units of frames and causes the display unit 16 to display the ultrasonic image.

The display unit 16 is a display device such as a liquid crystal display (LCD), a cathode-ray tube (CRT) display, an organic electronic luminescence (EL) display, or a plasma display. The display unit 16 sequentially and continuously displays the ultrasonic images stored in the frame memory (not illustrated) under the control of the control unit 11. In addition, the display unit 16 displays various operation screens or the like on the screen under the control of the control unit 11.

The storage unit 17 includes, for example, a hard disk drive (HDD), a semiconductor nonvolatile memory, or the like. The storage unit 17 stores various programs, data necessary for executing the programs, or the like.

The operation unit 18 includes various switches, function buttons, a trackball, a mouse, a keyboard, a touch panel, or the like. The operation unit 18 outputs an operation signal generated based on the operation by the user of the ultrasonic diagnostic apparatus 1 to the control unit 11.

Figure 2:
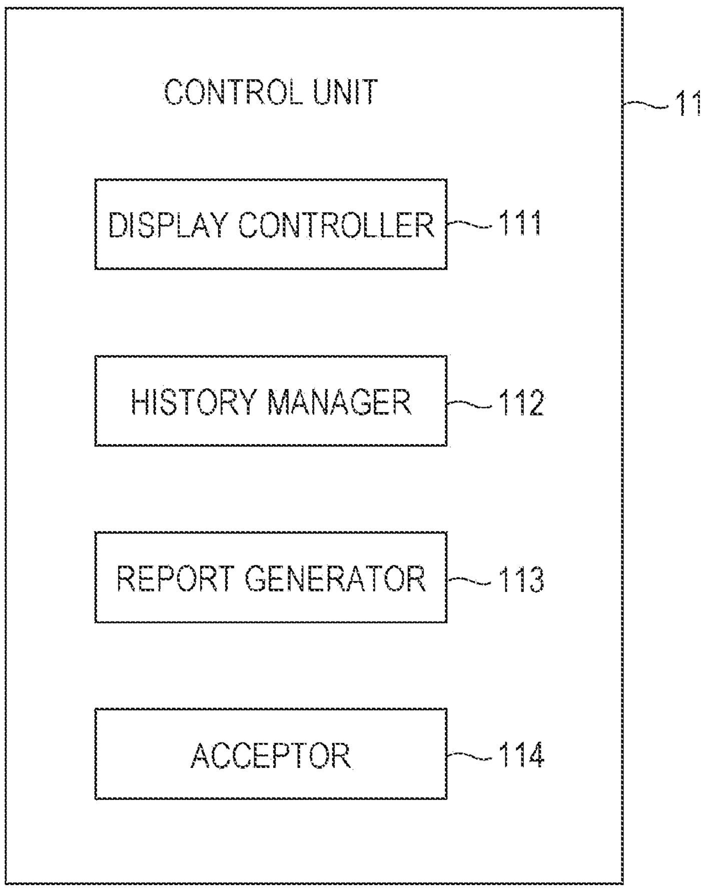
FIG. 2 is a diagram illustrating functional blocks included in a control unit.

FIG. 2 is a diagram illustrating functional blocks included in the control unit 11. As illustrated in FIG. 2, the control unit 11 includes a display controller 111, a history manager 112, a report generator 113, and an acceptor 114.

The display controller 111 generates a screen displayed on the display unit 16 based on the ultrasonic image or the like generated by the image processing unit 14. Examples of the screen displayed on the display unit 16 by the display controller 111 include a measurement screen for performing measurement using an ultrasonic image while keeping the ultrasonic image stationary, a report screen displaying a report summarizing measurement values, or the like.

In a case where an inspection of a certain subject (patient or the like) is performed using the ultrasonic diagnostic apparatus 1, a user such as a doctor appropriately performs diagnosis while viewing a real-time ultrasonic image based on an ultrasonic signal obtained from the subject. During diagnosis, when the user desires to perform various measurements related to a structure (an organ, a fetus, or the like) in the subject, the ultrasonic diagnostic apparatus 1 can transition to the measurement screen and perform various measurements on the ultrasonic image displayed on the measurement screen. In addition, in a case where the user desires to create a report by collecting measurement values obtained by measurement, the ultrasonic diagnostic apparatus 1 can transition to a report screen to edit and create the report.

Figure 3A:
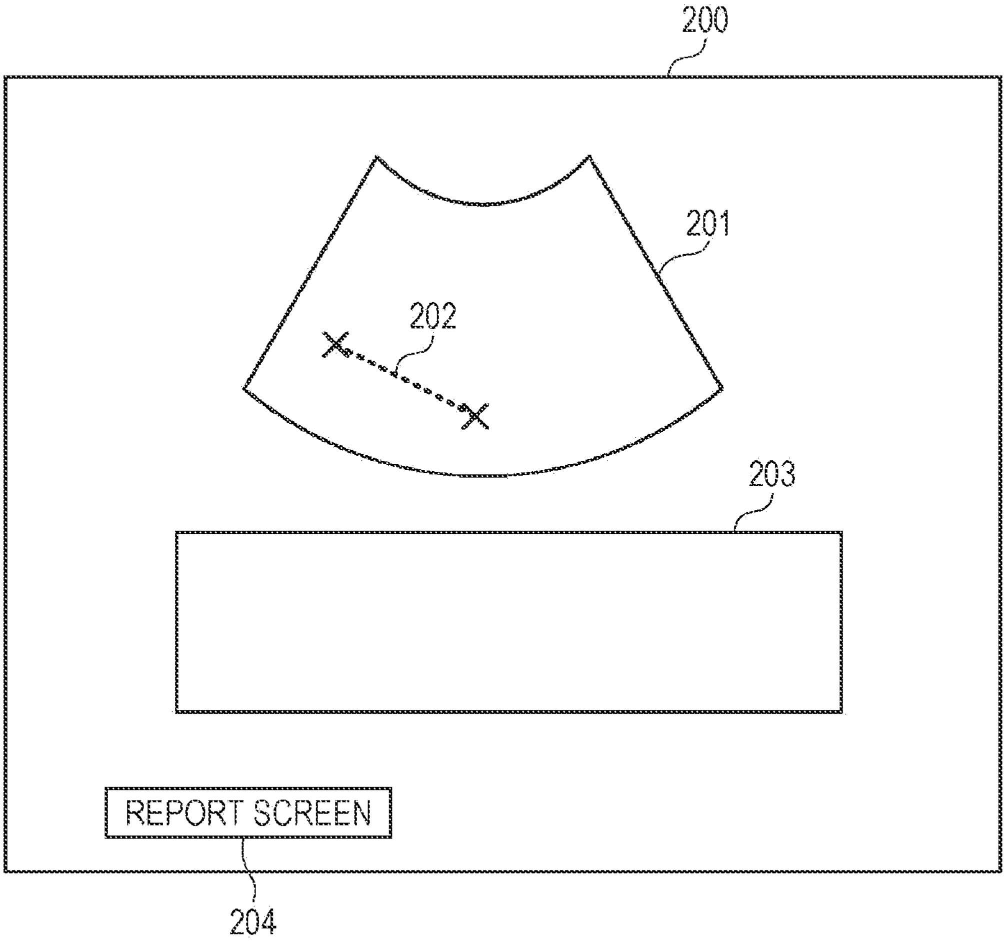
FIGS. 3A and 3B are diagrams for describing a measurement screen.
Figure 3B:
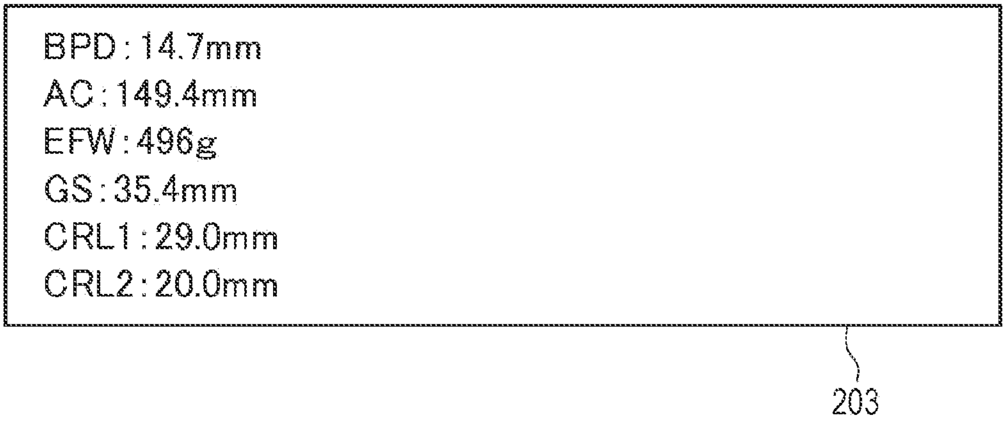

FIGS. 3A and 3B are diagrams for describing a measurement screen 200. FIG. 3A illustrates the entire measurement screen 200. The measurement screen 200 includes an ultrasonic image display field 201, a measurement scale 202, a measurement history display field 203, and a report screen display button 204.

The ultrasonic image display field 201 is a field for displaying, as a still image, an ultrasonic image of arbitrary one frame selected by the user from among ultrasonic images of a plurality of frames generated by the image processing unit 14. The ultrasonic image shows a structure of the subject.

The measurement scale 202 is a tool for measuring a measurement value related to the structure of the subject appearing in the ultrasonic image displayed in the ultrasonic image display field 201. In the present embodiment, as an example, the measurement scale 202 is a tool that measures a distance between arbitrary two points in a structure of a subject appearing in an ultrasonic image as a measurement value. As another example, the measurement scale 202 may be a tool that measures various measurement values such as an area, a volume, a speed, and a flow rate. The measurement scale 202 is displayed in the ultrasonic image display field 201. The measurement scale 202 is movable by a user's operation. In the example illustrated in FIG. 3A, only one measurement scale 202 is illustrated, but for example, a plurality of measurement scales 202 used for measuring a plurality of items (details will be described later) may be displayed in the measurement screen 200.

Note that, when the acceptor 114 to be described later accepts the correction or deletion of the position of the measurement scale 202, the display controller 111 corrects or deletes the position of the measurement scale 202 according to the user's operation. As a result, for example, in a case where there is a measurement scale arranged at a wrong position, the position can be corrected or the measurement scale can be deleted.

The measurement history display field 203 is a field for displaying a history of measurement values of various items. FIG. 3B illustrates an example of content displayed in the measurement history display field 203.

In the measurement using the measurement screen 200, various items can be measured depending on a structure target. For example, in the example illustrated in FIG. 3B, in a case where the target is a fetus, measurement values for each item such as biparietal diameter (BPD), abdominal circumference (AC), estimated infant weight (EFW), gestation sac (GS), and crown-rump length (CRL) are illustrated in the measurement history display field 203. In a case where the inspection target is not a fetus, the measurement value of an item different from the above example may be displayed in the measurement history display field 203. At the time of measurement, for example, when the user performs an operation to select an item, item names (labels) such as BPD and AC and a measurement value are displayed in the measurement history display field 203. In the example illustrated in FIG. 3B, a new measurement value is displayed as going downward.

Note that the user may perform measurement for the same item a plurality of times on the measurement screen 200. The plurality of times of measurement can be performed in a case where the previous measurement was insufficient (for example, the position specification of the measurement scale fails, the measurement value is abnormal, or the like), in a case where an item is erroneously measured (for example, an item of the BPD has been selected in order to measure the CRL), or the like.

In the measurement history display field 203, a plurality of measurement values is displayed for items measured a plurality of times. In the measurement history display field 203, in order to distinguish a plurality of times of measurements, for example, the number of times is assigned to the item name of the measurement value. In the example illustrated in FIG. 3B, two measurement values of "CRL1: 29.0 mm" and "CRL2: 20.0 mm" are illustrated as measurement values of CRLs for which measurement has been performed twice. The display of "CRL1" indicates the measurement value obtained by the first measurement, and the display of "CRL2" indicates the measurement value obtained by the second measurement.

In this manner, the measurement history display field 203 displays a history of measurement values measured during inspection of a certain subject. That is, in the measurement history display field 203, not only the measurement value of the item measured immediately before but also the measurement values of other items measured before the measurement value are displayed. In addition, a plurality of measurement values is displayed in the measurement history display field 203 in a case where measurement is performed a plurality of times. Note that, in a case where the measurement is performed three or more times, all the measurement values may be displayed in the measurement history display field 203, or only some (for example, the latest two) measurement values may be displayed.

The history information regarding the history of the measurement value displayed in the measurement history display field 203 of the measurement screen 200 is managed by the history manager 112 to be described later.

The description returns to FIG. 3A. The report screen display button 204 is a button for transitioning the display from the measurement screen 200 to a report screen 300 to be described later. Note that the report is, for example, a report of an inspection result for a certain patient. The report includes the measurement value measured on the measurement screen 200.

On the measurement screen 200 exemplified in FIG. 3A, the user can correct or delete an arbitrary display object included in the measurement screen 200 by an operation via the operation unit 18. On the measurement screen 200, the display object (hereinafter, it is described as a correction/deletion target object) to be corrected or deleted includes the measurement value for each item or the measurement scale 202 for each item displayed in the measurement history display field 203. When the user desires to perform correction or deletion on the measurement screen 200, the user selects a correction/deletion target object using the operation unit 18 and performs an operation of correcting or deleting the correction/deletion target object. When a correction or deletion operation is performed by the user, correction or deletion of the display object included in the measurement screen 200 is accepted by the acceptor 114 to be described later, and correction or deletion of the correction/deletion target object is executed by each functional block. Details of the operation of the ultrasonic diagnostic apparatus when correcting or deleting the correction/deletion target object will be described later.

Figure 4:
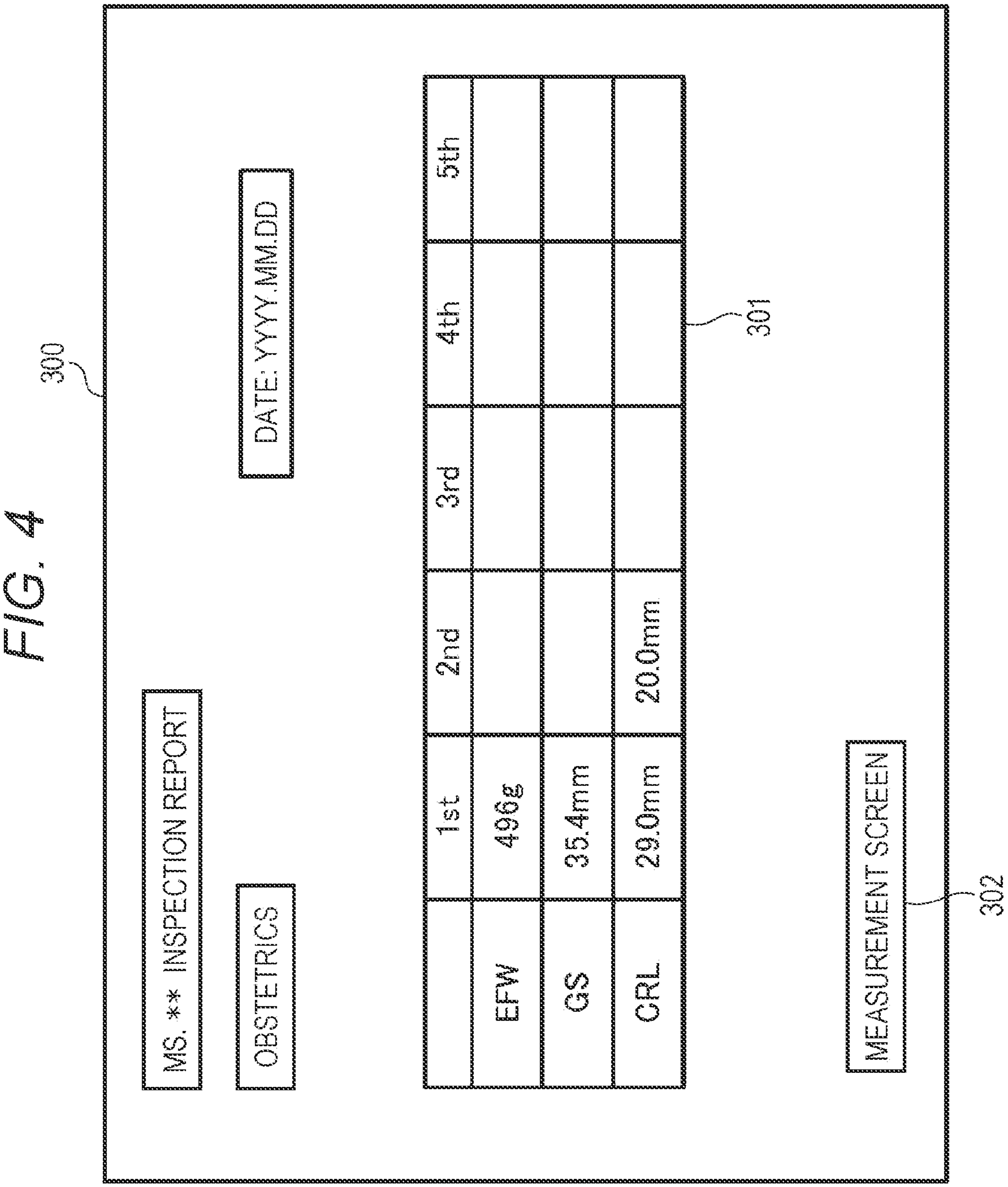
FIG. 4 is a diagram for describing a report screen.

FIG. 4 is a diagram for describing the report screen 300. The report screen 300 includes a measurement value display field 301 and a measurement screen display button 302.

The measurement value display field 301 is a field for displaying the measurement value measured on the measurement screen 200 for each item. Note that the measurement history display field 203 on the measurement screen 200 and the measurement value display field 301 on the report screen 300 may be different in display format, that is, the presence or absence of a frame line, the size of a frame, the size of a character, the font, or the like.

Note that the measurement value displayed in the measurement value display field 301 of the report screen 300 is managed by the report generator 113 described later. That is, in the ultrasonic diagnostic apparatus 1, measurement values are stored and managed separately in the history manager 112 and the report generator 113. In this specification, in order to distinguish between the measurement value managed by the history manager 112 and the measurement value managed by the report generator 113, the measurement value managed by the history manager 112 is referred to as a history measurement value, and the measurement value managed by the report generator 113 is referred to as a report measurement value.

In the example illustrated in FIG. 4, in the measurement value display field 301, a display field ("1st" field, "2nd" field, "3rd" field, "4th" field, and "5th" field) of measurement values of items for which a plurality of measurements has been performed is provided in advance. The first measurement value is displayed in the "1st" field, and the second measurement value is displayed in the "2nd" field. In a case where there is no corresponding measurement value, a blank field may be displayed. Note that, in the present disclosure, only the latest measurement value may be displayed for each item on the report screen.

The measurement screen display button 302 is a button for transitioning the display from the report screen 300 to the measurement screen 200.

In the report screen 300 illustrated in FIG. 4, similarly to the measurement screen 200 in FIG. 3A, the user can correct or delete an arbitrary display object included in the report screen 300 by an operation via the operation unit 18. The correction/deletion target object on the report screen 300 is a measurement value for each item displayed in the measurement history display field 203. When the user desires to perform correction or deletion on the report screen 300, the user selects a correction/deletion target object using the operation unit 18 and performs an operation of correcting or deleting the correction/deletion target object. When a correction or deletion operation is performed by the user, correction or deletion of the display object included in the report screen 300 is accepted by the acceptor 114 to be described later, and correction or deletion of the correction/deletion target object is executed by each functional block. Details of the operation of the ultrasonic diagnostic apparatus when correcting or deleting the correction/deletion target object will be described later.

The description returns to FIG. 2. The history manager 112 stores and manages the measurement value measured on the measurement screen 200 for each item for each subject.

The history manager 112 collects all the measurement values measured on the measurement screen 200 and manages them as history information. In the present disclosure, as described above, the measurement value included in the history information is described as a history measurement value, and is distinguished from the report measurement value managed by the report generator 113. The history information includes a plurality of measurement values for an item for which measurement has been performed a plurality of times. The display controller 111 displays the measurement history display field 203 illustrated in FIGS. 3A and 3B based on the history information.

The history manager 112 generates history information every time an inspection on a new subject is started, and holds and manages the history information until the inspection on the subject is completed. The history manager 112 adds a new measurement value to the history information each time new measurement is performed on the subject under inspection. In a case where the inspection for the subject under inspection is completed, the history manager 112 may discard the history information, or may store the history information in association with the name, identification number, or the like of the subject in the database of the storage unit 17, for example.

In addition, when correction or deletion of the measurement value is accepted by the acceptor 114 to be described later and the measurement value is corrected or deleted, the history manager 112 reflects the measurement value changed by the correction in the history information or deletes the deleted measurement value from the history information without leaving a history of the correction or deletion. As a result, for example, in a case where an erroneous measurement value is included in the history information, the measurement value can be corrected or deleted.

For example, when an erroneous measurement value is corrected, in a case where the history manager 112 leaves the measurement value before correction in the history information, the measurement value before correction is continuously displayed also in the measurement history display field 203, which may cause confusion of the user who browses the measurement screen 200. In order to avoid such a situation, the history manager 112 does not leave the measurement value corrected or deleted as described above in the history information, and reflects the correction or deletion in the history information. Details of the operation when correcting or deleting the measurement value of the ultrasonic diagnostic apparatus will be described later.

The report generator 113 generates the report illustrated in the report screen 300 of FIG. 4 based on the measurement value measured by the measurement scale 202 on the measurement screen 200. The information regarding the report generated by the report generator 113 is managed as report information. As described above, the report generator 113 manages the measurement value included in the report as a report measurement value independent of the history measurement value included in the history information managed by the history manager 112.

The acceptor 114 accepts correction or deletion of a display object displayed on the measurement screen 200 or the report screen 300 according to an operation of the user via the operation unit 18. In a case where the user selects a display object and performs an operation for correction or deletion on the operation unit 18 on the measurement screen 200 or the report screen 300 illustrated in FIG. 3A, the acceptor 114 accepts correction or deletion of the selected display object.

When accepting the correction or deletion of the display object, the acceptor 114 causes the functional block that manages the display object designated as the target to be corrected or deleted to respond to the correction or deletion of the display object. At the same time, the acceptor 114 causes the functional block that manages another display object to respond to the correction or deletion to cause not only the display object designated as the target to be corrected or deleted but also another display object related to the display object to be corrected or deleted as necessary.

Hereinafter, three specific examples will be described.

First Specific Example

First specific example is an example of a case where the acceptor 114 accepts correction or deletion of the measurement scale 202 in the ultrasonic image display field 201. In a case where the user performs an operation of correcting or deleting the measurement scale 202 via the operation unit 18, the acceptor 114 accepts correction or deletion of the measurement scale 202. The acceptor 114 that has accepted the correction or deletion of the measurement scale 202 first causes the display controller 111 to correct or delete the measurement scale 202 that has accepted the correction or deletion. In addition, the acceptor 114 causes the history manager 112 to correct or delete the history measurement value corresponding to the measurement scale 202 corrected or deleted among the history measurement values included in the history information. Further, the acceptor 114 causes the report generator 113 to correct or delete the report measurement value corresponding to the measurement scale 202 corrected or deleted among the report measurement values included in the measurement value display field 301 (see FIG. 4) of the report screen 300.

When the history measurement value included in the history information managed by the history manager 112 is corrected or deleted, the measurement value displayed in the measurement history display field 203 (see FIGS. 3A and 3B) of the measurement screen 200 is also corrected or deleted.

Figure 5A:
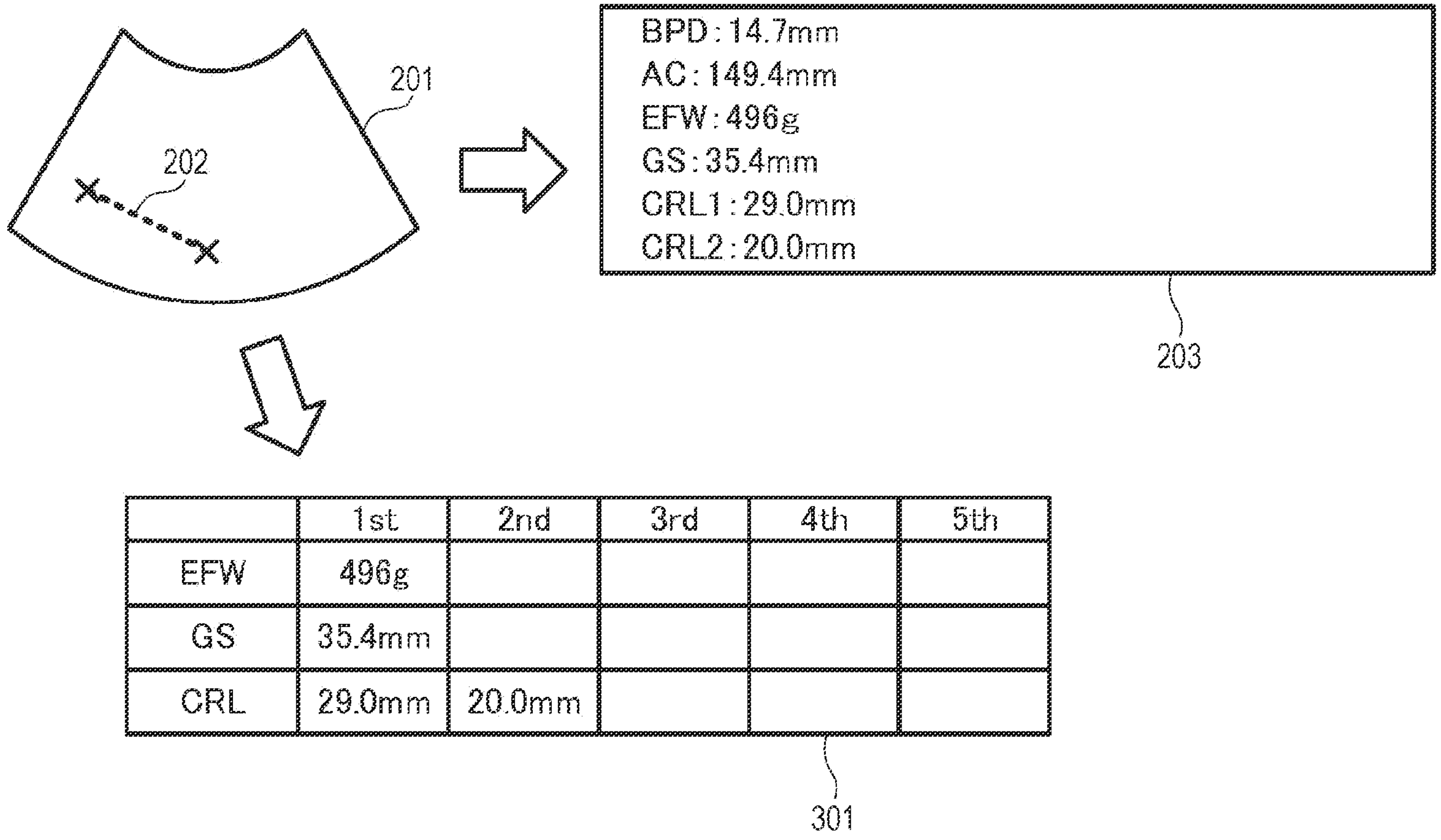
FIGS. 5A and 5B are diagrams illustrating respective display objects according to a first specific example.
Figure 5B:
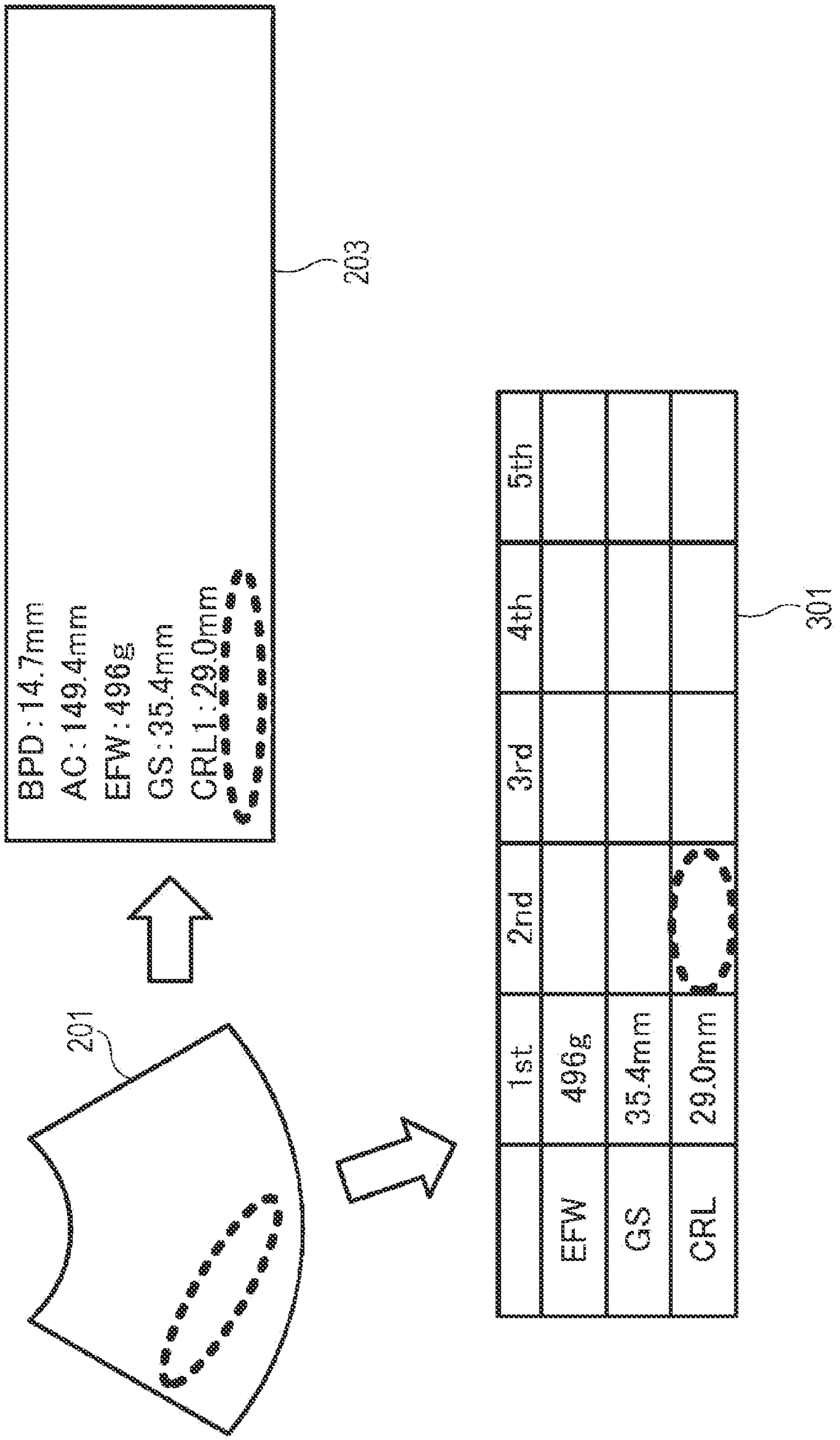

FIGS. 5A and 5B are diagrams illustrating respective display objects according to the first specific example. FIG. 5B illustrates the ultrasonic image display field 201 from which the measurement scale 202 has been deleted, and the measurement history display field 203 and the measurement value display field 301 from which the measurement value (CRL2) corresponding to the deleted measurement scale 202 has been deleted. FIG. 5A illustrates the ultrasonic image display field 201, the measurement history display field 203, and the measurement value display field 301 before the measurement scale 202 is deleted. In FIG. 5B, the position of the deleted display object is surrounded by a broken line.

Second Specific Example

Second specific example is an example of a case where the acceptor 114 accepts correction or deletion of the history measurement value managed by the history manager 112. Note that the correction or deletion of the history measurement value is accepted when the user performs an operation of correcting or deleting the measurement value displayed in the measurement history display field 203 of the measurement screen 200.

In a case where the user performs an operation of correcting or deleting the measurement value displayed in the measurement history display field 203 via the operation unit 18, the acceptor 114 causes the history manager 112 to correct or delete the history measurement value corresponding to the measurement value whose correction or deletion has been accepted among the history measurement values included in the history information. In addition, the acceptor 114 causes the display controller 111 to correct or delete the measurement scale 202 corresponding to the corrected or deleted measurement value among the measurement scales 202 displayed in the ultrasonic image display field 201. Further, the acceptor 114 causes the report generator 113 to correct or delete the report measurement value corresponding to the measurement scale 202 corrected or deleted among the report measurement values included in the report screen 300.

Figure 6A:
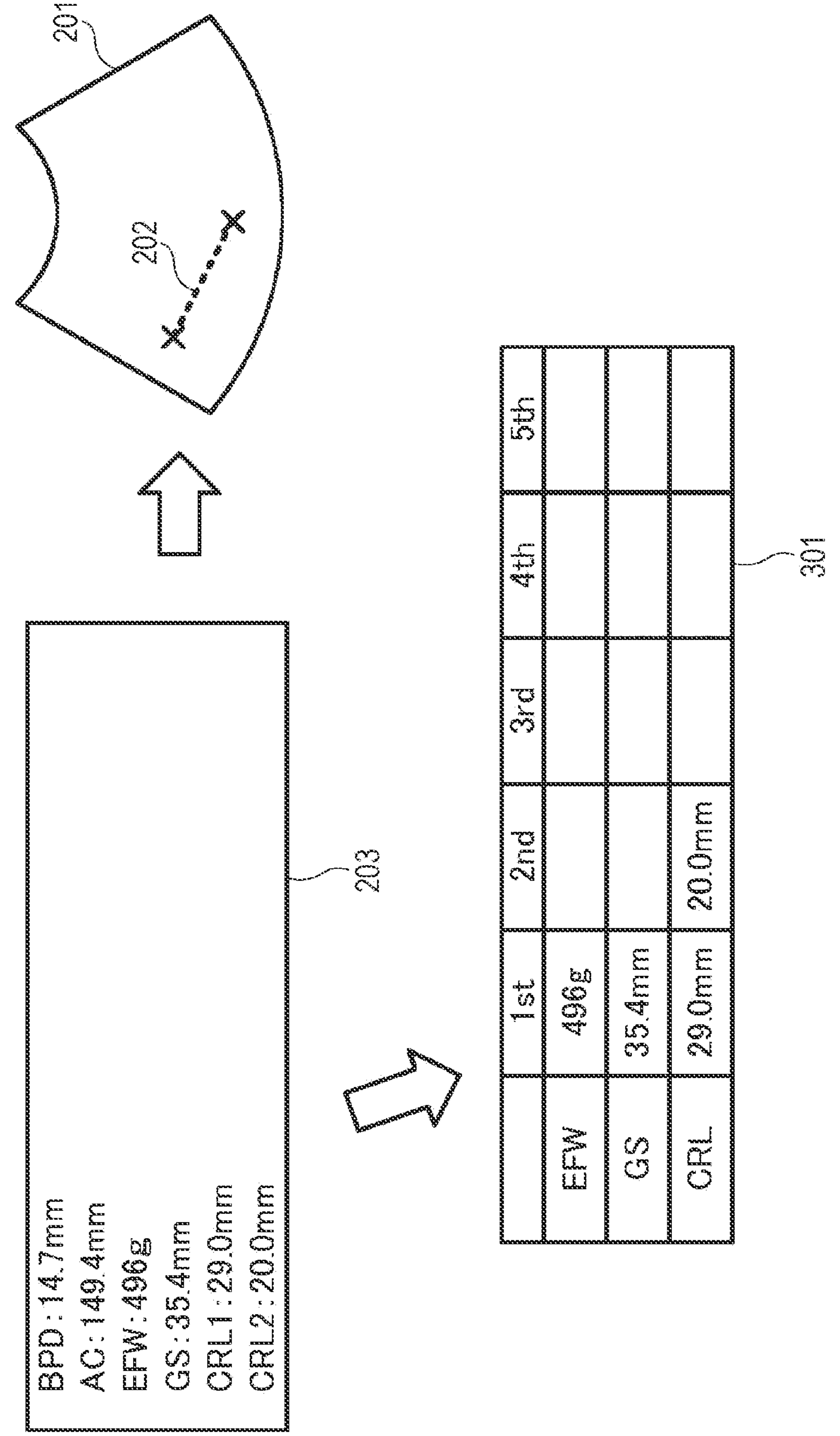
FIGS. 6A and 6B are diagrams illustrating respective display objects according to a second specific example.
Figure 6B:
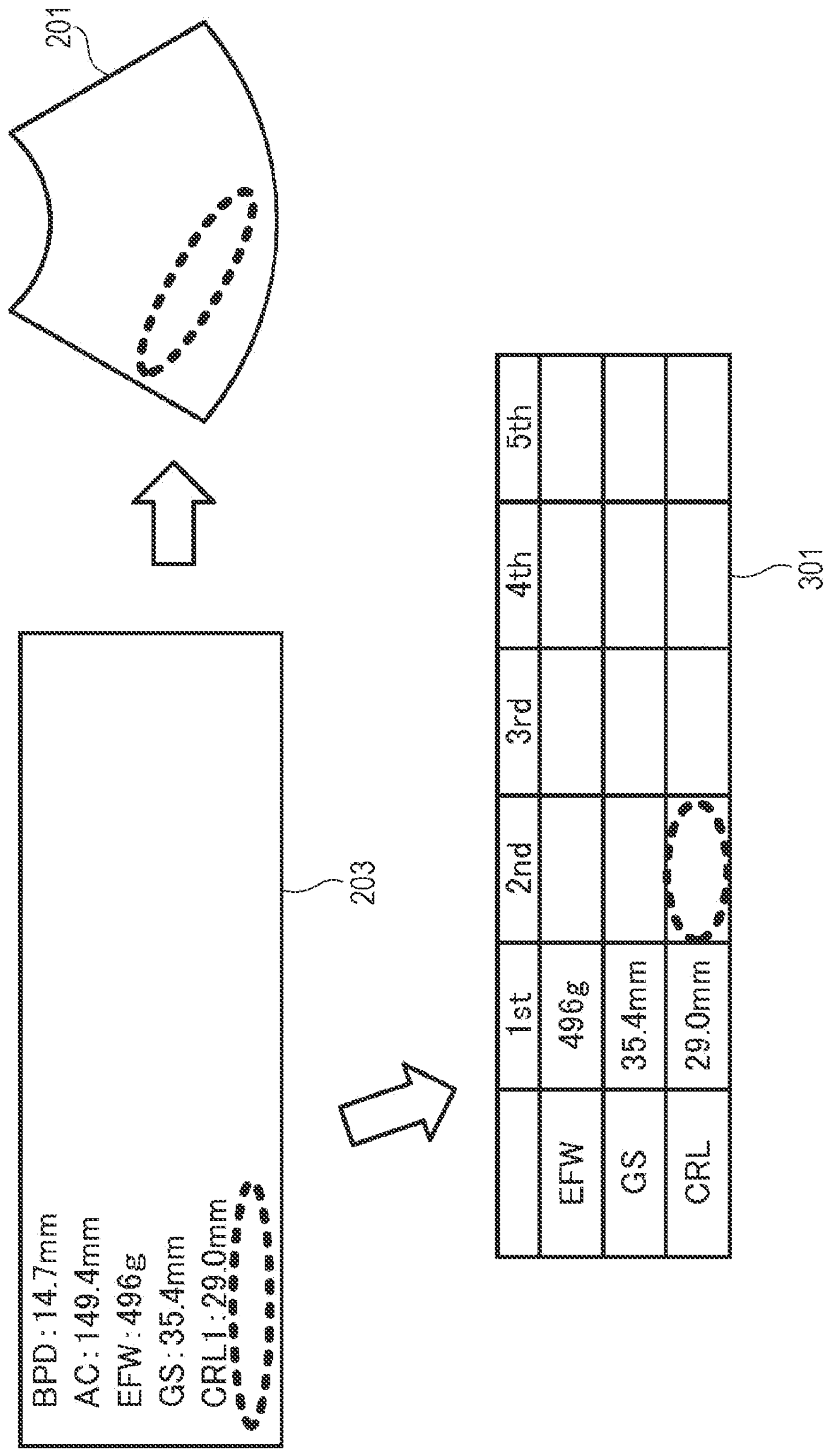

FIGS. 6A and 6B are diagrams illustrating respective display objects according to the second specific example. FIG. 6B illustrates the measurement history display field 203 from which the measurement value (CRL2) has been deleted, the ultrasonic image display field 201 from which the measurement scale 202 corresponding to the deleted measurement value has been deleted, and the measurement value display field 301 from which the report measurement value corresponding to the deleted measurement value has been deleted. FIG. 6A illustrates the measurement history display field 203, the measurement value display field 301, and the ultrasonic image display field 201 before the measurement value displayed in the measurement history display field 203 is deleted. In FIG. 6B, the position of the deleted display object is surrounded by a broken line.

Third Specific Example

Third specific example is an example of a case where the acceptor 114 accepts correction or deletion of the report measurement value managed by the report generator 113. Note that the correction or deletion of the report measurement value is accepted when the user performs an operation of correcting or deleting the measurement value displayed in the measurement value display field 301 of the report screen 300.

In a case where the user performs an operation of correcting or deleting the measurement value displayed in the measurement value display field 301 via the operation unit 18, the acceptor 114 causes the report generator 113 to correct or delete the report measurement value corresponding to the measurement value whose correction or deletion has been accepted among the report measurement values. In addition, the acceptor 114 causes the display controller 111 to correct or delete the measurement scale 202 corresponding to the corrected or deleted report measurement value among the measurement scales 202 displayed in the ultrasonic image display field 201. Further, the acceptor 114 causes the history manager 112 to correct or delete the history measurement value corresponding to the report measurement value corrected or deleted among the history measurement values included in the history information.

Figure 7A:
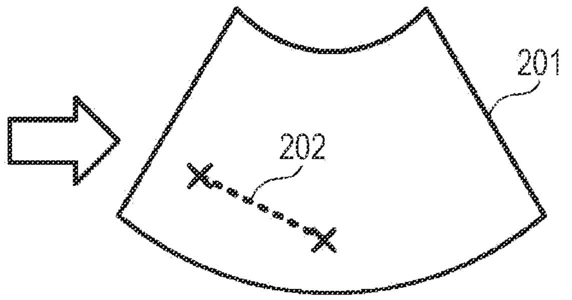
FIGS. 7A and 7B are diagrams illustrating respective display objects according to a third specific example.
Figure 7B:
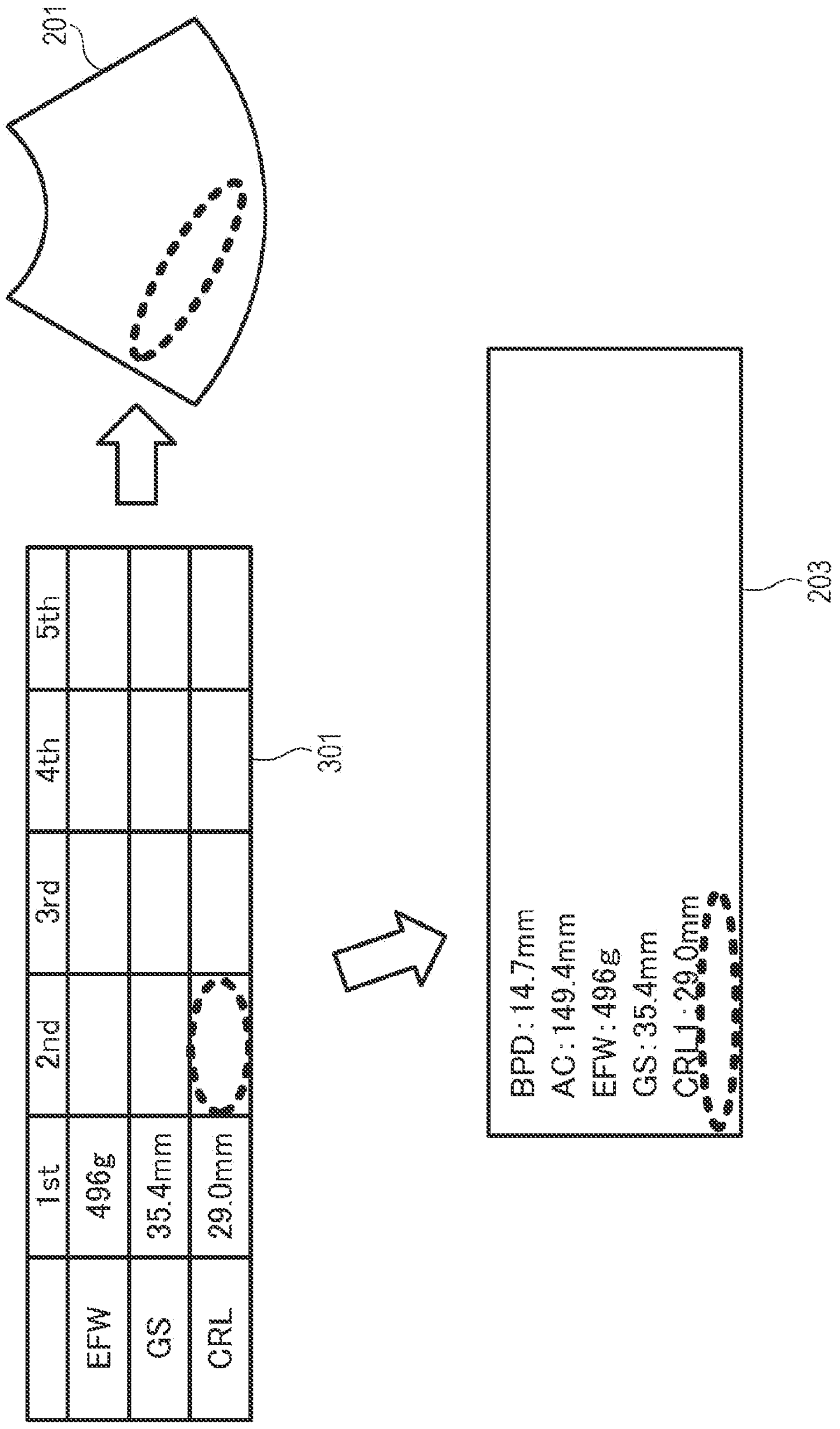

FIGS. 7A and 7B are diagrams illustrating respective display objects according to the third specific example. FIG. 7B illustrates the measurement value display field 301 from which the measurement value (CRL2) has been deleted, the measurement value display field 301 from which the measurement value corresponding to the deleted measurement value has been deleted, and the ultrasonic image display field 201 from which the measurement scale 202 corresponding to the deleted measurement value has been deleted. FIG. 7A illustrates the measurement value display field 301, the measurement history display field 203, and the ultrasonic image display field 201 before the measurement value displayed in the measurement value display field 301 is deleted. In FIG. 7B, the position of the deleted display object is surrounded by a broken line.

As described in the above specific example, in a case where the acceptor 114 accepts correction or deletion of any one selected correction deletion target object among the measurement scale 202, the history measurement value, and the correction/deletion target object of the report measurement value, correction or deletion of the selected correction/deletion target object is executed, and correction or deletion of an unselected correction/deletion target object is also executed. In this manner, since the ultrasonic diagnostic apparatus 1 executes the correction or deletion of the three types of correction/deletion target objects only by the user's operation for correcting or deleting any one type of correction/deletion target object, the user does not need to separately perform correction or deletion operations of different correction/deletion target objects. Therefore, the operation at the time of correction or deletion is simplified, and usability can be improved.

In particular, in a case where any one of the measurement values in the history of the measurement values displayed in the measurement history display field 203 of the measurement screen 200 is corrected or deleted, the history manager 112 does not leave a history related to correction or deletion and leaves only the corrected or deleted history measurement value in the history information. Therefore, it is possible to avoid a situation in which an erroneous measurement value is continuously displayed in the measurement history display field 203 and the user is confused.

For example, in a case where the ultrasonic diagnostic apparatus 1 according to the present embodiment is connected to another medical device installed in a medical facility or another computer such as an electronic medical record server by a communication method such as Digital Imaging and Communications in Medicine (DICOM), the management information managed by the history manager 112 and the report information generated by the report generator 113 may be configured to be automatically transmitted to another computer. Even in such a case, in the ultrasonic diagnostic apparatus 1, the history information and the report information are managed independently of each other, and the history measurement value before correction or deletion does not remain in the history information. Therefore, it is possible to avoid a situation that causes confusion of a user or the like who checks data of the ultrasonic diagnostic apparatus 1 using another computer.

Figure 8:
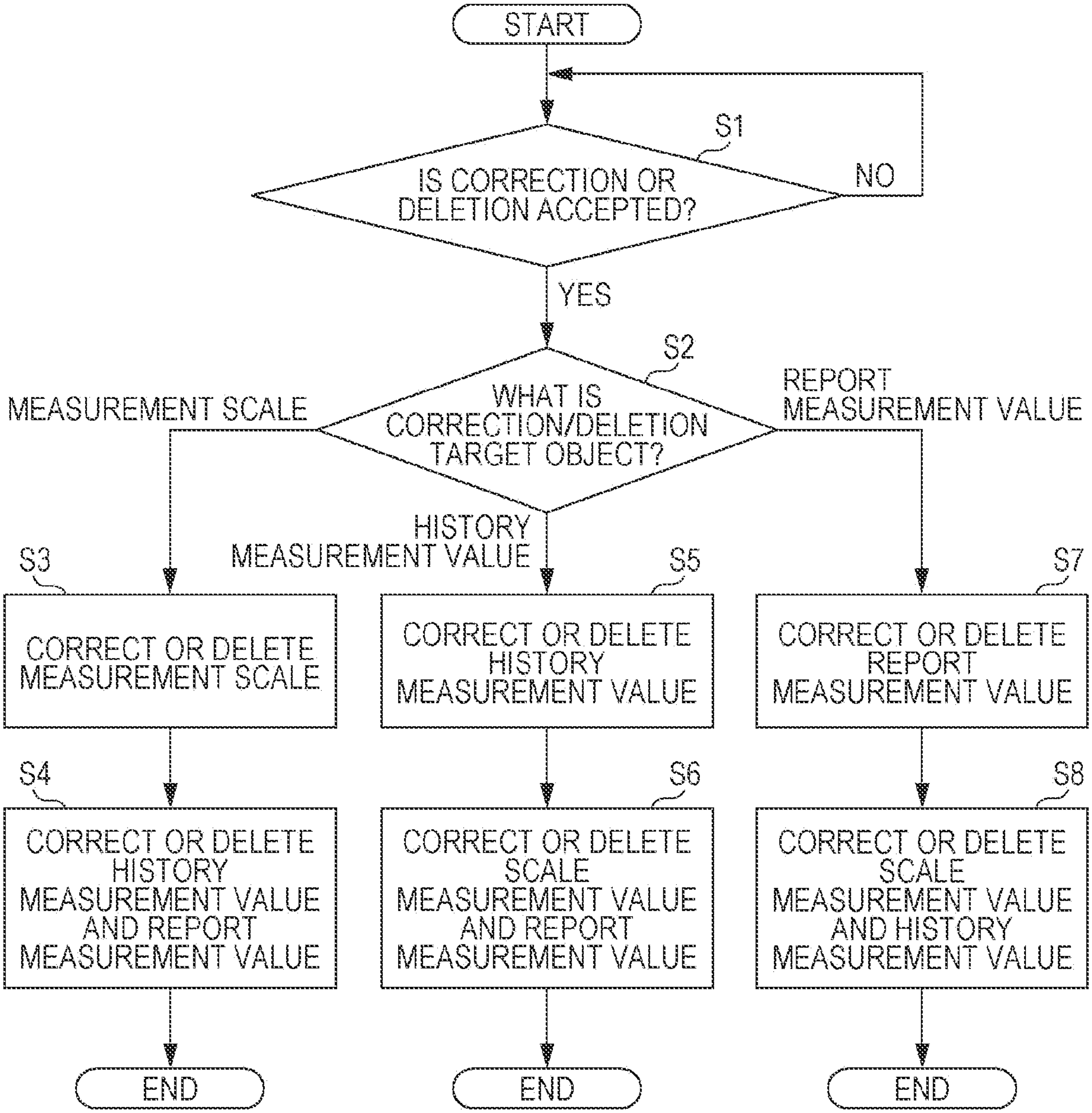
FIG. 8 is a flowchart illustrating an operation example at a time of correcting or deleting a display object in an ultrasonic diagnostic apparatus 1.

Hereinafter, an operation example of the ultrasonic diagnostic apparatus 1 will be described. FIG. 8 is a flowchart illustrating an operation example at a time of correcting or deleting a display object in the ultrasonic diagnostic apparatus 1.

In step S1, the acceptor 114 determines whether or not correction or deletion of any of the display objects on the measurement screen 200 or the report screen 300 has been accepted. In a case where it is determined that the correction or deletion has been accepted (step S1: YES), the processing proceeds to step S2, and otherwise (step S1: NO), the processing of step S1 is repeated.

In step S2, the acceptor 114 determines whether the display object (correction/deletion target object) whose correction or deletion has been accepted is the measurement scale 202, the measurement value (history measurement value) displayed in the measurement history display field 203, or the report measurement value. In a case where the correction/deletion target object is the measurement scale 202, the processing proceeds to step S3. In a case where the correction/deletion target object is the history measurement value, the processing proceeds to step S5. In a case where the correction/deletion target object is the report measurement value, the processing proceeds to step S7.

In step S3, the acceptor 114 causes the display controller 111 to correct or delete the position of the measurement scale 202 that has accepted the correction or deletion. Then, in step S4, the acceptor 114 causes the history manager 112 to correct or delete the history measurement value corresponding to the measurement scale 202 that has been corrected or deleted, and causes the report generator 113 to correct or delete the report measurement value corresponding to the measurement scale 202 that has been corrected or deleted.

In step S5, the acceptor 114 causes the history manager 112 to correct or delete the history measurement value corresponding to the measurement value whose correction or deletion has been accepted. Then, in step S6, the acceptor 114 causes the display controller 111 to correct or delete the measurement scale 202 corresponding to the history measurement value that has been corrected or deleted, and causes the report generator 113 to correct or delete the report measurement value corresponding to the measurement scale 202 that has been corrected or deleted.

In step S7, the acceptor 114 causes the report generator 113 to correct or delete the report measurement value whose correction or deletion has been accepted. Then, in step S8, the acceptor 114 causes the display controller 111 to correct or delete the measurement scale 202 corresponding to the report measurement value that has been corrected or deleted, and causes the history manager 112 to correct or delete the history measurement value corresponding to the report measurement value that has been corrected or deleted.

<Modification>

The above-described exemplary embodiments are one aspect of the present disclosure, and the present disclosure is not limited to the contents of the exemplary embodiments.

In the embodiment, the ultrasonic diagnostic apparatus that performs measurement based on an ultrasonic image has been described, but the present disclosure can be applied to a medical image processing apparatus that performs measurement using various medical images in addition to an ultrasonic image.

The present disclosure can be applied to a medical image processing apparatus that performs measurement using a medical image.

According an embodiment of the present disclosure, the discrepancy between the display content and the history data can be eliminated at the time of correcting the measurement value.

Although embodiments of the present invention have been described and illustrated in detail, the disclosed embodiments are made for purposes of illustration and example only and not limitation. The scope of the present invention should be interpreted by terms of the appended claims

What is claimed is:

1. A medical image processing apparatus comprising a hardware processor that displays a measurement image including a measurement object and a measurement scale for measuring a measurement value related to the measurement object in a manner that the measurement scale is superimposed on the measurement image, manages history information related to the measurement value, and accepts correction or deletion of a position of the measurement scale, wherein the hardware processor corrects or deletes a history measurement value corresponding to the measurement scale having the position corrected or deleted among history measurement values included in the history information in a case where the position of the measurement scale is corrected or deleted.

2. The medical image processing apparatus according to claim 1, wherein the hardware processor accepts correction or deletion of any of the history measurement values, and the hardware processor corrects or deletes the position of the measurement scale corresponding to the corrected or deleted history measurement value among displayed measurement scales in a case where the history measurement value is corrected or deleted.

3. The medical image processing apparatus according to claim 1, wherein the hardware processor generates a report including the measurement value measured by the measurement scale, and the hardware processor corrects or deletes a report measurement value corresponding to the measurement scale having the position corrected or deleted among report measurement values included in the report in a case where the position of the measurement scale is corrected or deleted.

4. The medical image processing apparatus according to claim 3, wherein the hardware processor accepts correction or deletion of any of the report measurement values, and the hardware processor corrects or deletes the position of the measurement scale corresponding to the corrected or deleted report measurement value among measurement scales being displayed in a case where the report measurement value is corrected or deleted.

5. The medical image processing apparatus according to claim 3, wherein the hardware processor corrects or deletes the history measurement value corresponding to a corrected or deleted report measurement value in a case where the report measurement value is corrected or deleted.

6. The medical image processing apparatus according to claim 3, wherein the hardware processor corrects or deletes the report measurement value corresponding to a corrected or deleted history measurement value in a case where the history measurement value is corrected or deleted.

7. The medical image processing apparatus according to claim 1, wherein the correction or deletion is a correction or deletion of a position of the measurement scale on the measurement image, and the hardware processor corrects or deletes a history measurement value corresponding to the position of the measurement scale that has been corrected or deleted among the history measurement values included in the history information.

8. The medical image processing apparatus according to claim 7, wherein the history information includes one or more history measurement values for an item for which the measuring using the measurement scale has been performed.

9. A control method executed by a computer included in a medical image processing apparatus, the control method comprising:

displaying a measurement image including a measurement object and a measurement scale for measuring a measurement value related to the measurement object in a manner that the measurement scale is superimposed on the measurement image;

managing history information related to the measurement value; and correcting or deleting a history measurement value corresponding to the measurement scale having a position whose correction or deletion is accepted among history measurement values included in the history information in a case where correction or deletion of the position of the measurement scale is accepted.

10. A non-transitory recording medium storing a computer readable program causing a computer included in a medical image processing apparatus to perform:

displaying a measurement image including a measurement object and a measurement scale for measuring a measurement value related to the measurement object in a manner that the measurement scale is superimposed on the measurement image;

managing history information related to the measurement value; and correcting or deleting a history measurement value corresponding to the measurement scale having a position whose correction or deletion is accepted among history measurement values included in the history information in a case where correction or deletion of the position of the measurement scale is accepted.

* * * * *